(12) United States Patent
Hosaka et al.

(10) Patent No.: US 10,590,211 B2
(45) Date of Patent: Mar. 17, 2020

(54) METHOD FOR PRODUCING SOLID CATALYST COMPONENT FOR OLEFIN POLYMERIZATION, OLEFIN POLYMERIZATION CATALYST, METHOD FOR PRODUCING OLEFIN POLYMERIZATION CATALYST, AND METHOD FOR PRODUCING OLEFIN POLYMER

(71) Applicant: TOHO TITANIUM CO., LTD., Chigasaki-shi, Kanagawa (JP)

(72) Inventors: Motoki Hosaka, Chigasaki (JP); Toshihiko Sugano, Chigasaki (JP); Tsutomu Uzawa, Chigasaki (JP)

(73) Assignee: TOHO TITANIUM CO., LTD., Chigasaki-shi (JP)

( * ) Notice: Subject to any disclaimer, the term of this patent is extended or adjusted under 35 U.S.C. 154(b) by 132 days.

(21) Appl. No.: 15/846,789

(22) Filed: Dec. 19, 2017

(65) Prior Publication Data
US 2019/0185597 A1    Jun. 20, 2019

(51) Int. Cl.
*C08F 110/06* (2006.01)
(52) U.S. Cl.
CPC .................... *C08F 110/06* (2013.01)
(58) Field of Classification Search
CPC ......... C08F 110/06; C08F 10/02; C08F 10/06
USPC ........................................................ 526/125
See application file for complete search history.

(56) References Cited

U.S. PATENT DOCUMENTS 6,521,560 B1    2/2003 Kojoh et al.
2003/0050184 A1 *   3/2003 Job .................... C07F 7/003
                                                    502/150

FOREIGN PATENT DOCUMENTS

JP    2013-18865 A      1/2013
JP    2013018865 A  *   1/2013
JP    2014040577 A  *   3/2014

* cited by examiner

*Primary Examiner* — Michael Bernshteyn
(74) *Attorney, Agent, or Firm* — Westerman, Hattori, Daniels & Adrian, LLP

(57) ABSTRACT

A method for producing a solid catalyst component includes bringing a magnesium compound, a titanium halide compound, and one or more internal electron donor compounds into contact with each other to effect a reaction; washing the resulting product with a first inert organic wash solvent that does not have reactivity with the titanium halide compound, and has a solubility parameter (SP) of 8.0 to 9.0; washing the resulting intermediate product in the absence of the titanium halide compound with a second inert organic wash solvent that includes a hydrocarbon compound and does not have reactivity with the titanium halide compound, but has a solubility parameter (SP) of more than 9.0; and washing the resulting product in the absence of the titanium halide compound with a third inert organic wash solvent that does not have reactivity with the titanium halide compound, and has a solubility parameter (SP) of less than 8.0.

12 Claims, No Drawings

METHOD FOR PRODUCING SOLID CATALYST COMPONENT FOR OLEFIN POLYMERIZATION, OLEFIN POLYMERIZATION CATALYST, METHOD FOR PRODUCING OLEFIN POLYMERIZATION CATALYST, AND METHOD FOR PRODUCING OLEFIN POLYMER

TECHNICAL FIELD

The present invention relates to a method for producing a solid catalyst component for olefin polymerization, a method for producing an olefin polymerization catalyst, and a method for producing an olefin polymer.

BACKGROUND ART

A solid catalyst component that can produce an olefin polymer that exhibits high stereoregularity in high yield has been desired in order to achieve a reduction in thickness (weight) and an increase in strength with respect to a resin molded article. For example, Patent Literature 1 (JP-A-2013-018865) discloses a method for producing a solid catalyst component that brings a magnesium compound, a tetravalent titanium halide compound, and an electron donor compound into contact with each other in the presence of an inert hydrocarbon compound solvent to effect a reaction, and washes the resulting solid product with a hydrocarbon compound solvent, wherein the solid product is washed at least once with a hydrocarbon compound solvent that includes a halogen-containing hydrocarbon compound.

CITATION LIST

Patent Literature

Patent Literature 1: JP-A-2013-018865

SUMMARY OF INVENTION

Technical Problem

In recent years, a solid catalyst component capable of producing an olefin polymer that exhibits high stereoregularity and high rigidity has been desired in order to obtain a high physical strength required for manufacturing a large molded product. According to the above method, however, since a Ti species having low stereospecificity remains in the solid catalyst component, it is difficult to achieve both high stereoregularity and high rigidity although the stereoregularity of the resulting polymer is improved to some extent. Therefore, a further improvement has been desired.

Specifically, a solid catalyst component for olefin polymerization that capable of producing an olefin polymer that exhibits both high stereoregularity and high rigidity has been desired.

In view of the above situation, the inventors conducted extensive studies in order to solve the above problem. As a result, the inventors found that the above problem can be solved by bringing a magnesium compound, a tetravalent titanium halide compound, and an electron donor compound into contact with each other in the presence of an inert organic solvent to effect a reaction, and sequentially washing the resulting solid product with three solvents that differ with respect to solubility. This finding has led to the completion of the invention.

Solution to Problem

Specifically, the invention provides a method for producing a solid catalyst component for olefin polymerization including:

bringing a magnesium compound, a titanium halide compound, and one or more internal electron donor compounds into contact with each other in the presence of an inert organic solvent to effect a reaction;

washing the resulting product with a first inert organic wash solvent that does not have reactivity with the titanium halide compound, and has a solubility parameter (SP) of 8.0 to 9.0;

washing the resulting intermediate product one or more times in the absence of the titanium halide compound with a second inert organic wash solvent that comprises a hydrocarbon compound and does not have reactivity with the titanium halide compound, but has a solubility parameter (SP) of more than 9.0; and washing the resulting product one or more times in the absence of the titanium halide compound with a third inert organic wash solvent that does not have reactivity with the titanium halide compound, and has a solubility parameter (SP) of less than 8.0.

Advantageous Effects of Invention

According to the invention, it is possible to efficiently remove a Ti species that forms an active site having low stereospecificity from the solid catalyst component for olefin polymerization, and produce a polymer that exhibits high stereoregularity and significantly improved mechanical properties (e.g., rigidity) by polymerizing an olefin using the solid catalyst component.

DESCRIPTION OF EMBODIMENTS

The method for producing a solid catalyst component for olefin polymerization according to the invention includes:

bringing a magnesium compound, a titanium halide compound, and one or more internal electron donor compounds into contact with each other in the presence of an inert organic solvent to effect a reaction;

washing the resulting product with a first inert organic wash solvent that does not have reactivity with the titanium halide compound, and has a solubility parameter (SP) of 8.0 to 9.0;

washing the resulting intermediate product one or more times in the absence of the titanium halide compound with a second inert organic wash solvent that comprises a hydrocarbon compound and does not have reactivity with the titanium halide compound, but has a solubility parameter (SP) of more than 9.0; and washing the resulting product one or more times in the absence of the titanium halide compound with a third inert organic wash solvent that does not have reactivity with the titanium halide compound, and has a solubility parameter (SP) of less than 8.0.

The magnesium compound (hereinafter may be referred to as "component (a)") that is used in connection with the method for producing a solid catalyst component for olefin polymerization according to the invention may be one or more magnesium compounds selected from a dialkoxymagnesium, a magnesium dihalide, an alkoxymagnesium halide, and the like.

Among these magnesium compounds, a dialkoxymagnesium and a magnesium dihalide are preferable. Specific examples of the dialkoxymagnesium and the magnesium dihalide include dimethoxymagnesium, diethoxymagnesium, dipropoxymagnesium, dibutoxymagnesium, ethoxymethoxymagnesium, ethoxypropoxymagnesium, butoxyethoxymagnesium, magnesium dichloride, magnesium dibromide, magnesium diiodide, and the like. Among these, diethoxymagnesium and magnesium dichloride are particularly preferable.

The titanium halide compound (hereinafter may be referred to as "component (b)") that is used in the first step included in the method for producing a solid catalyst component for olefin polymerization according to the invention is not particularly limited. It is preferable that the titanium halide compound be one or more compounds selected from a titanium halide and an alkoxytitanium halide represented by the following general formula (3).

$$Ti(OR^4)_rX_{4-r} \quad (3)$$

wherein $R^4$ is an alkyl group having 1 to 4 carbon atoms, X is (independently) a halogen atom (e.g., chlorine atom, bromine atom, or iodine atom), and r is an integer from 0 to 3, provided that a plurality of $OR^4$ are either identical to or different from each other when a plurality of $OR^4$ are present.

Examples of the titanium halide compound include a titanium tetrahalide such as titanium tetrachloride, titanium tetrabromide, and titanium tetraiodide, and an alkoxytitanium halide such as methoxytitanium trichloride, ethoxytitanium trichloride, propoxytitanium trichloride, n-butoxytitanium trichloride, dimethoxytitanium dichloride, diethoxytitanium dichloride, dipropoxytitanium dichloride, di-n-butoxytitanium dichloride, trimethoxytitanium chloride, triethoxytitanium chloride, tripropoxytitanium chloride, and tri-n-butoxytitanium chloride. Among these, a titanium tetrahalide is preferable, and titanium tetrachloride is particularly preferable.

These tetravalent titanium compounds may be used either alone or in combination.

The internal electron donor compound (hereinafter may be referred to as "component (b)") that is used in the first step included in the method for producing a solid catalyst component for olefin polymerization according to the invention may be a known compound selected from organic compounds that include two or more electron donor sites (e.g., hydroxy group (—OH), carbonyl group (>C=O), ether linkage (—OR), amino group (—NH$_2$, —NHR, or —NHRR'), cyano group (—CN), isocyanate group (—N=C=O), and amide linkage (—C(=O)NH— or —C(=O)NR—)) and do not include silicon. A carbonyl group (>C=O) includes an aldehyde group (—C(=O)H), a carboxy group (—C(=O)OH), a keto group (—C(=O)R), a carbonate group (—O—C(=O)O—), an ester linkage (—C(=O)O—), a urethane linkage (—NH—C(=O)O—), and the like.

Among these, an ester compound such as a polycarboxylic acid ester, and an ether compound such as a diether and an ether carbonate are preferable. These internal electron donor compounds may be used either alone or in combination.

The first inert organic wash solvent for washing that is used in connection with the method for producing a solid catalyst component for olefin polymerization according to the invention does not have reactivity with the titanium halide compound, and has a solubility parameter (SP) of 8.0 to 9.0.

It is preferable that the first inert organic wash solvent for washing have a solubility parameter (SP) of 8.1 to 9.0, more preferably 8.1 to 8.9, and particularly preferably 8.4 to 8.9.

Specific examples of a compound that satisfies the above condition include an aromatic hydrocarbon compound having 6 to 20 carbon atoms, a linear or branched aliphatic hydrocarbon compound having 10 to 20 carbon atom and an alicyclic hydrocarbon compound having 6 to 20 carbon atoms. Among these, an aromatic hydrocarbon compound having 6 to 12 carbon atoms such as toluene (SP=8.9), ethylbenzene (SP=8.8), and xylene(SP=8.8), and an alicyclic hydrocarbon compound having 6 to 12 carbon atoms such as cyclohexane (SP=8.2) and decalin (SP=8.8), are preferable, an aromatic hydrocarbon compound having 6 to 12 carbon atoms, such as toluene, ethylbenzene, and xylene, are more preferable, and toluene and ethylbenzene are particularly preferable.

Note that the solubility parameter (SP) is a value defined by regular solution theory proposed by Hildebrand. From this theory, the solubility parameter (SP) is calculated using the following expression as a square root (cal/cm$^3$)$^{0.5}$ of the heat of vaporization required for a liquid having a volume of 1 cm$^3$ to vaporize.

$$\text{Solubility parameter } (\delta) = \{(\Delta H - RT) \div V\}^{0.5}$$

where, $\Delta H$ is the molar heat of vaporization (cal/mol), R is a gas constant (m$^2$·kg/(s$^2$·K·mol)), T is absolute temperature (K), and V is molar volume (cm$^3$/mol).

The second inert organic wash solvent that is used in connection with the method for producing a solid catalyst component for olefin polymerization according to the invention comprises a hydrocarbon compound and does not have reactivity with the titanium halide compound, but has a solubility parameter (SP) of more than 9.0. It is preferable that the second inert organic wash solvent have a solubility parameter (SP) of 9.1 to 10.9, more preferably 9.1 to 10.6, and particularly preferably 9.5 to 10.2.

Specific examples of a compound that satisfies the above condition include a halogen-containing aromatic hydrocarbon compound having 6 to 12 carbon atoms, a linear or branched halogen-containing aliphatic hydrocarbon compound having 4 to 12 carbon atoms, and a halogen-containing alicyclic hydrocarbon compound having 7 to 12 carbon atoms. Among these, a halogen-containing aromatic hydrocarbon compound having 6 to 12 carbon atoms and a linear halogen-containing aliphatic hydrocarbon compound having 4 to 6 carbon atoms are preferable, a halogen-containing aromatic hydrocarbon compound having 6 to 12 carbon atoms such as chlorobenzene (SP=9.8), o-dichlorobenzene (SP=10.0), dibromoethane (SP=10.4), and 1-bromonaphthalene (SP=10.6), is more preferable, and chlorobenzene and o-dichlorobenzene are particularly preferable.

It is possible to efficiently remove a Ti species that remains in the solid catalyst component for olefin polymerization, and easily forms an active site having low stereospecificity, by washing the resulting intermediate product with the second inert organic wash solvent comprising a hydrocarbon compound whose solubility parameter (SP) falls within the above range in the absence of the titanium halide compound.

The third inert organic wash solvent that is used in connection with the method for producing a solid catalyst component for olefin polymerization according to the invention does not have reactivity with the titanium halide compound, and has a solubility parameter (SP) of less than 8.0. It is preferable that the third inert organic wash solvent have a solubility parameter (SP) of 6.3 to 7.9, more preferably 7.0 to 7.9, and particularly preferably 7.3 to 7.6.

Specific examples of a compound that satisfies the above condition include a linear or branched aliphatic hydrocarbon compound having 6 to 10 carbon atoms and an alicyclic hydrocarbon compound having 5 to 6 carbon atoms. Among these, a linear aliphatic hydrocarbon compound having 6 to 8 carbon atoms and an alicyclic hydrocarbon compound having 6 carbon atoms are preferable, an aliphatic hydrocarbon compound having 6 to 8 carbon atoms, such as n-hexane (SP=7.3), n-heptane (SP=7.4), n-octane (SP=7.6), decane (SP=6.6) and dodecane (SP=7.9) is more preferable, and n-hexane and n-heptane are particularly preferable.

BEST MODE FOR CARRYING OUT THE INVENTION

A preferable embodiment of the method for producing a solid catalyst component for olefin polymerization according to the invention includes an embodiment (hereinafter may be referred to as "embodiment a") for producing a solid catalyst component for olefin polymerization including:

suspending a magnesium compound in an inert organic solvent in a liquid state at ordinary temperature to prepare a suspension;

then bringing this suspension into contact with a titanium halide compound to effect a reaction;

contacting one or more electron donor compounds to effect a reaction before or after bringing this suspension into contact with a titanium halide compound to effect a reaction;

washing the resulting solid product with a first inert organic wash solvent that does not have reactivity with the titanium halide compound, and has a solubility parameter (SP) of 8.0 to 9.0;

then washing the resulting intermediate product one or more times in the absence of the titanium halide compound with a second inert organic wash solvent in the absence of the titanium halide compound, the second inert organic wash solvent comprises a hydrocarbon compound and does not have reactivity with the titanium halide compound, but has a solubility parameter (SP) of more than 9.0; and further washing one or more times in the absence of the titanium halide compound with a third inert organic wash solvent that does not have reactivity with the titanium halide compound, and has a solubility parameter (SP) of less than 8.0.

In embodiment a, the inert organic solvent used when suspending the above-mentioned magnesium compound and contacting the respective components to effect a reaction includes one or more selected from saturated hydrocarbon compounds such as hexane, heptane and cyclohexane or aromatic hydrocarbon compounds such as benzene, toluene, xylene and ethylbenzene. Among these, one or more selected from aromatic hydrocarbon compounds having a boiling point of 80 to 150° C. and being in a liquid state at ordinary temperature, or specifically one or more selected from toluene, xylene and ethylbenzene are used preferably.

In embodiment a, before washing the obtained solid product with the first inert organic wash solvent one or both of a tetravalent titanium halide compound and an electron donor compound may be further brought into contact repeatedly. In this case, it is possible to preferably improve polymerization activity and stereoregularity of the obtained solid catalyst component.

In embodiment a, it is preferable that the contact and reaction of the respective components such as a magnesium compound, a titanium halide compound and an electron donor compound are performed with stirring in a container with a stirrer under an inert gas atmosphere where moisture and the like are removed.

In embodiment a, the temperature at the time of contacting the respective components such as a magnesium compound, a titanium halide compound and an electron donor compound may be in a comparatively low temperature region near a room temperature in the case of mixing and stirring with simple contact or of carrying out modifying processing by distribution or suspension, but a 40 to 130° C. temperature region is preferable when a target product is obtained by reacting the respective components at the same time as or after the contact.

In embodiment a, it is hard to fully advance the reaction and to obtain a solid catalyst component having sufficient performance when the temperature at the time of the reaction is less than 40° C., while reaction control tends to be difficult because evaporation of the solvent becomes remarkable, etc. when the temperature at the time of the reaction exceeds 130° C. Moreover, the reaction time is preferably one minute or more, more preferably 10 minutes or more, and still more preferably 30 minutes or more.

In addition, a preferable embodiment of the method for producing a solid catalyst component for olefin polymerization according to the invention includes an embodiment (hereinafter may be referred to as "embodiment b") for producing a solid catalyst component for olefin polymerization including:

mixing dialkoxy magnesium, one or more electron donor compounds, and an inert organic solvent having a boiling point of 80 to 150° C. and being in a liquid state at ordinary temperature to prepare a suspension;

then performing a reaction processing (first reaction processing) at 40 to 130° C. after contacting and mixing this suspension with a mixed solution consisting of a tetravalent titanium halide compound and an inert organic solvent having a boiling point of 80 to 150° C. and being in a liquid state at ordinary temperature, at a temperature of −20 to 130° C.;

performing a reaction processing (second reaction processing), after the first reaction processing, by heating the resulting solid product and a tetravalent titanium halide compound and optionally one or more electron donor compounds in the presence of an aromatic hydrocarbon compound having a boiling point of 80 to 150° C. and being in a liquid state at ordinary temperature with the temperature increasing to 40 to 130° C.;

washing the resulting solid product with a first inert organic wash solvent that does not have reactivity with the titanium halide compound, and has a solubility parameter (SP) of 8.0 to 9.0;

then washing the resulting intermediate product one or more times in the absence of the titanium halide compound with a second inert organic wash solvent, that comprises an organic solvent and does not have reactivity with the titanium halide compound, but has a solubility parameter (SP) of more than 9.0; and further washing one or more times in the absence of the titanium halide compound with a third inert organic wash solvent that does not have reactivity with the titanium halide compound, and has a solubility parameter (SP) of less than 8.0.

In embodiment b, the inert organic solvent used when suspending the above-mentioned magnesium compound and contacting and reacting the respective components includes solvents equivalent to one having a boiling point of 80 to 150° C. and being in a liquid state at ordinary temperature among those mentioned in the explanation of the above-mentioned embodiment a.

In embodiment b, after completion of the first reaction processing, the second reaction processing may be performed after operation of washing the obtained solid product with a hydrocarbon compound in a liquid state at ordinary temperature is repeated 1 to 10 times.

In embodiment b, the internal electron donor compound contacted and reacted in the first reaction processing includes one or more selected from aromatic dicarboxylic diesters, etc.

The preferable combinations of the electron donor compound used in the first reaction processing and the electron donor compound used in the second reaction processing are as follows (In the following combinations, the "electron donor compound used in the first reaction processing" and the "electron donor compound used in the second reaction processing" are indicated in this order. For example, "an aromatic dicarboxylic acid diester and an aromatic dicarboxylic acid diester" means that the electron donor compound used in the first reaction processing is an aromatic dicarboxylic acid diester and the electron donor compound used in the second reaction processing is also an aromatic dicarboxylic acid diester).

(1) an aromatic dicarboxylic acid diester and an aromatic dicarboxylic acid diester, (2) an aromatic dicarboxylic acid diester and ether carbonates, (3) an aromatic dicarboxylic acid diester and an aliphatic dicarboxylic acid diester, (4) an aromatic dicarboxylic acid diester and a cycloalkanedicarboxylic acid diester, (5) an aromatic dicarboxylic acid diester and a cycloalkenedicarboxylic acid diester, (6) an aromatic dicarboxylic acid diester and diethers.

In embodiment b, between the first reaction processing and the second reaction processing or before washing with the first inert organic wash solvent after completion of the second reaction processing, one or both of the tetravalent titanium halide compound and electron donor compound may be further contacted repeatedly. In this case, it is possible to preferably improve polymerization activity and stereoregularity of the obtained solid catalyst component.

Moreover, in embodiment b, after contacting and mixing a suspension containing the above-mentioned dialkoxy magnesium and one or more electron donor compounds with a mixed solution containing a tetravalent titanium halide compound, it is desirable to perform an aging reaction at low temperature before carrying out the reaction processing (the first reaction processing) at 40 to 130° C.

The temperature at the time of the above-mentioned aging reaction is preferably −20° C. or more and less than 40° C., more preferably −10 to 30° C., and still more preferably −10 to 20° C. Moreover, the reaction time of the above-mentioned aging reaction is preferably 1 minute to 6 hours, more preferably 5 minutes to 4 hours, and still more preferably 10 minutes to 3 hours.

The reaction temperatures at the time of the first reaction processing or the second reaction processing are 40 to 130° C. in both cases, preferably 70 to 130° C., and more preferably 80 to 120° C. The reaction time at the time of the first reaction processing or the second reaction processing is preferably 30 minutes to 6 hours, more preferably 30 minutes to 5 hours, and still more preferably 1 to 4 hours.

Furthermore, a preferable embodiment of the method for producing a solid catalyst component for olefin polymerization according to the invention includes an embodiment (hereinafter may be referred to as "embodiment c") for producing a solid catalyst component for olefin polymerization including:

performing a first step that brings a magnesium compound, a tetravalent titanium halide compound, and one or more first internal electron donor compounds into contact with each other to effect a reaction, followed by washing;

performing a second step that brings a tetravalent titanium halide compound and one or more second internal electron donor compounds into contact with the resulting intermediate product to effect a reaction, followed by washing;

performing a third step that brings one or more third internal electron donor compounds into contact with the resulting intermediate product to effect a reaction, followed by washing with a first inert organic wash solvent that does not have reactivity with the titanium halide compound, and has a solubility parameter (SP) of 8.0 to 9.0;

then washing the resulting intermediate product one or more times in the absence of the titanium halide compound with a second inert organic wash solvent, that comprises a hydrocarbon compound and does not have reactivity with the titanium halide compound, but has a solubility parameter (SP) of more than 9.0; and further washing one or more times in the absence of the titanium halide compound with a third inert organic wash solvent that does not have reactivity with the titanium halide compound, and has a solubility parameter (SP) of less than 8.0.

According to the preferred embodiment c, the method for producing a solid catalyst component for olefin polymerization according to the invention includes:

performing a first step that brings a magnesium compound, a titanium halide compound, and a first internal electron donor compound into contact with each other to effect a reaction, and washes the resulting product;

performing a second step that brings a second internal electron donor compound into contact with the resulting intermediate product (i) in the presence of the titanium halide compound to effect a reaction, and washes the resulting product;

Optionally performing a third step that brings a third internal electron donor compound into contact with the resulting intermediate product (ii) in the absence of the titanium halide compound to effect a reaction, and washes the resulting product with the first inert organic wash solvent that does not have reactivity with the titanium halide compound, and has a solubility parameter (SP) of 8.0 to 9.0;

performing a fourth step that washes the resulting intermediate product (iii) one or more times with a second inert organic wash solvent that comprises a hydrocarbon compound and does not have reactivity with the titanium halide compound, but has a solubility parameter (SP) of more than 9.0; and washing the resulting product one or more times with a third inert organic wash solvent that does not have reactivity with the titanium halide compound, and has a solubility parameter (SP) of less than 8.0.

A component (I) according to the invention is produced as described below.

In the first step, the magnesium compound, the titanium halide compound, and the first internal electron donor compound are brought into contact with each other to effect a reaction, and the resulting product is washed with the first inert organic wash solvent that has a solubility parameter (SP) of 8.0 to 9.0.

The magnesium compound, the titanium halide compound, and the first inert organic wash solvent are the same as those mentioned above in connection with the method for producing a solid catalyst component for olefin polymerization according to the invention.

The first internal electron donor compound may be one or more compounds selected from aromatic dicarboxylic acid diesters (phthalic acid diester and substituted phthalic acid diester) represented by the following general formula (4).

wherein $R^5$ is an alkyl group having 1 to 8 carbon atoms or a halogen atom, provided that a plurality of $R^1$ are either identical to or different from each other when a plurality of $R^5$ are present, $R^6$ and $R^7$ are an alkyl group having 1 to 12 carbon atoms, provided that $R^6$ and $R^7$ are either identical to or different from each other, and j that represents the number of substituents $R^5$, is 0, 1, or 2, provided that the two $R^1$ are either identical or different when j is 2.

In the second step, the titanium halide compound and optionally the second internal electron donor compound are brought into contact with the intermediate product obtained by the first step to effect a reaction, and the resulting product is washed with the first inert organic wash solvent that has a solubility parameter (SP) of 8.0 to 9.0.

The titanium halide compound and the first inert organic wash solvent are the same as those mentioned above in connection with the method for producing a solid catalyst component for olefin polymerization according to the invention. The second internal electron donor compound may be one or more compounds selected from those mentioned above in connection with the method for producing a solid catalyst component for olefin polymerization according to the invention. More specifically, an ester compound such as a polycarboxylic acid ester, and an ether compound such as a diether and an ether carbonate, are preferable, and an aromatic dicarboxylic acid diester (phthalic acid diester and substituted phthalic acid diester) is particularly preferable.

Optionally in the third step, the third internal electron donor compound is brought into contact with the intermediate product obtained by the second step in the absence of the titanium halide compound to effect a reaction, and the resulting product is washed with the first inert organic wash solvent that has a solubility parameter (SP) of 8.0 to 9.0.

The first inert organic wash solvent is the same as those mentioned above in connection with the method for producing a solid catalyst component for olefin polymerization according to the invention.

The third internal electron donor compound may be one or more compounds selected from those mentioned above in connection with the method for producing a solid catalyst component for olefin polymerization according to the invention.

More specifically, an ester compound such as a polycarboxylic acid ester, and an ether compound such as a diether and an ether carbonate, are preferable, and an aliphatic dicarboxylic acid diester and an aromatic dicarboxylic acid diester (phthalic acid diester and substituted phthalic acid diester) are particularly preferable.

The method for producing a solid catalyst component for olefin polymerization according to embodiment c of the invention may preferably be implemented as described below.

In the first step, a spherical magnesium compound is suspended in an inert organic solvent to prepare a suspension, the suspension at −20 to 130° C., before or after bringing the tetravalent titanium halide compound into contact with the suspension, and the reaction product is washed with an inert organic solvent to obtain a solid reaction product (a), it is preferable to effect a low-temperature aging reaction before or after bringing the first internal electron donor compound into contact with the suspension;

in the second step, the tetravalent titanium halide compound and the second internal electron donor compound are brought into contact with the reaction product (i) obtained by the first step at 20 to 130° C. (preferably 30 to 120° C., and more preferably 80 to 110° C.) to effect a reaction, and the reaction product is washed with an inert organic solvent to obtain a solid reaction product ( ) The above operation (i.e., contact with the tetravalent titanium halide compound and washing) may be repeated a plurality of times;

in the third step, the third internal electron donor compound is brought into contact with the reaction product (ii) obtained by the second step at 20 to 130° C. (preferably 30 to 120° C., and more preferably 80 to 110° C.) in the presence of an inert organic solvent, and the resulting product is washed with the first inert organic wash solvent that has a solubility parameter (SP) of 8.0 to 9.0;

performing a fourth step that washes the resulting intermediate product (iii) one or more times in the absence of the titanium halide compound with a second inert organic wash solvent that comprises a hydrocarbon compound and does not have reactivity with the titanium halide compound, but has a solubility parameter (SP) of more than 9.0; and washing the resulting product one or more times with a third inert organic wash solvent that does not have reactivity with the titanium halide compound, and has a solubility parameter (SP) of less than 8.0.

The method for producing a solid catalyst component for olefin polymerization according to embodiment c of the invention utilizes such as an aromatic dicarboxylic acid diester as the first internal electron donor compound.

Preferred combinations of the first internal electron donor compound, the second internal electron donor compound, and the third internal electron donor compound are shown below;

(1) a combination of an aromatic dicarboxylic acid diester, an aromatic dicarboxylic acid diester, and an aromatic dicarboxylic diester, (2) a combination of an aromatic dicarboxylic acid diester, an aromatic dicarboxylic acid diester or an ether carbonate, and an ether carbonate, (3) a combination of an aromatic dicarboxylic acid diester, an aromatic dicarboxylic acid diester or an aliphatic dicarboxylic acid diester, and an dicarboxylic acid diester, (4) a combination of an aromatic dicarboxylic acid diester, an aromatic dicarboxylic acid diester or a cycloalkanedicarboxylic acid diester, and a cycloalkanedicarboxylic acid diester, (5) a combination of an aromatic dicarboxylic acid diester, an aromatic dicarboxylic acid diester or a cycloalkenedicarboxylic acid diester, and a cycloalkenedicarboxylic acid diester, and (6) a combination of an aromatic dicarboxylic acid diester, an aromatic dicarboxylic acid diester or a diether, and a diether, are preferable as a combination of the first internal electron donor compound, the second internal electron donor compound, and the third internal electron donor compound.

When any of the above combinations (see (1) to (6)) is used as a combination of the first internal electron donor compound, the second internal electron donor compound, and the third internal electron donor compound when implementing the method for producing a solid catalyst component for olefin polymerization according to one embodiment of the invention, it is possible to easily produce an olefin homopolymer or copolymer that exhibits a high MFR and excellent stereo regularity.

In the method for producing a solid catalyst component for olefin polymerization of the present invention, the usage ratio of each compound cannot be generally specified since it changes with preparation methods of the solid catalyst component. However, for example, 0.5 to 100 mol of titanium halide compound per mol of magnesium compound is preferable, 0.5 to 50 mol is more preferable, and 1 to 10 mol is still more preferable. As for the electron donor compound, 0.01 to 10 mol per mol of magnesium compound is preferable, 0.01 to 1 mol is more preferable, and 0.02 to 0.6 mol is still more preferable.

In the method for producing a solid catalyst component for olefin polymerization according to the invention, a solid product obtained by bringing a magnesium compound, a titanium halide compound and one or more internal electron donor compounds into contact with each other to effect a reaction is sequentially washed with the first inert organic wash solvent to the third inert organic wash solvent each having a specified solubility parameter (SP).

When washing with the first inert organic wash solvent to the third inert organic wash solvent, the washing temperature is preferably 0 to 120° C., more preferably 10 to 110° C., and still more preferably 20 to 100° C. Moreover, when washing with the first inert organic wash solvent to the third inert organic wash solvent, the number of times of washing is preferably 1 to 20 times, more preferably 1 to 15 times, and still more preferably 1 to 10 times.

In the method for producing a solid catalyst component for olefin polymerization according to the invention, by sequentially washing with (1) the first inert organic wash solvent having a solubility parameter (SP) of 8.0 to 9.0, (2) the second inert organic wash solvent comprising a hydrocarbon compound having a solubility parameter (SP) of more than 9.0, and (3) the third inert organic wash solvent having a solubility parameter (SP) of less than 8.0, it becomes easy to balance the contents of the respective composition components such as the first internal electron donor compound and the titanium compound in the resulting solid catalyst component for olefin polymerization, and it becomes easy to form a Ti active site having stereoregularity.

In the method for producing a solid catalyst component for olefin polymerization according to the invention, without the washing step with (1) the first inert organic wash solvent having a solubility parameter (SP) of 8.0 to 9.0, it becomes difficult to balance the contents of the respective composition components such as the first internal electron donor compound and the titanium compound in the resulting solid catalyst component for olefin polymerization.

Moreover, in the method for producing a solid catalyst component for olefin polymerization according to the invention, without the washing step with (3) the third inert organic wash solvent having a solubility parameter (SP) of less than 8.0, a large amount of titanium compound that is not contributed to polymerization activity remains.

In the method for producing a solid catalyst component for olefin polymerization according to the invention, without the washing step with (2) the second inert organic wash solvent comprising a hydrocarbon compound having a solubility parameter (SP) of more than 9.0, when polymerizing olefin using the obtained solid catalyst component for olefin polymerization, it becomes difficult to improve stereoregularity of the resulting polymer.

The magnesium atom content in the solid catalyst component for olefin polymerization obtained by the production method according to the invention is preferably 10 to 30 wt %, more preferably 10 to 25 wt %, and yet more preferably 15 to 25 wt %.

The titanium atom content in the solid catalyst component is preferably 0.5 to 4.5 wt %, more preferably 0.5 to 3.5 wt %, and still more preferably 0.7 to 2.0 wt %.

The halogen atom content in the solid catalyst component is preferably 20 to 75 wt %, more preferably 30 to 70 wt %, and yet more preferably 40 to 65 wt %.

The content of the first internal electron donor compound in the solid catalyst component is preferably 3 to 25 wt %, more preferably 5 to 20 wt %, and particularly preferably 8 to 18 wt %.

Optionally, the content of the second internal electron donor compound in the solid catalyst component is preferably 1 to 20 wt %, more preferably 1 to 15 wt %, and particularly preferably 1 to 10 wt %.

Optionally, the content of the third internal electron donor compound in the solid catalyst component is preferably 1 to 15 wt %, more preferably 1 to 10 wt %, and particularly preferably 1 to 8 wt %.

The total content of the first internal electron donor compound, the second internal electron donor compound, and the third internal electron donor compound in the solid catalyst component is preferably 5 to 30 wt %, more preferably 8 to 25 wt %, and particularly preferably 10 to 25 wt %.

In order to ensure that the solid catalyst component for olefin polymerization obtained by the production method according to the invention exhibits well-balanced overall performance, it is preferable that the titanium content be 0.5 to 2.0 wt %, the magnesium content be 15 to 25 wt %, the halogen atom content be 45 to 65 wt %, the content of the first internal electron donor compound be 8 to 18 wt %, optionally the content of the second internal electron donor compound be 1 to 10 wt %, and optionally the content of the third internal electron donor compound be 1 to 8 wt %.

Polymerization Catalyst

An olefin polymerization catalyst according to the invention is described below.

The olefin polymerization catalyst according to the invention is produced by bringing a solid catalyst component for olefin polymerization obtained by the production method according to the invention, an organoaluminum compound represented by the following general formula (1), and an external electron donor compound into contact with each other.

$$R^1_p AlQ_{3-p} \qquad (1)$$

wherein $R^1$ is an alkyl group having 1 to 6 carbon atoms, Q is a hydrogen atom or a halogen atom, and p is a real number that satisfies $0 < p \le 3$.

The details of the solid catalyst component for olefin polymerization according to the invention have been described above.

The organoaluminum compound represented by the general formula (I) may be one or more compounds selected from triethylaluminum, diethylaluminum chloride, triisobutylaluminum, diethylaluminum bromide, and diethylaluminum hydride. Among these, triethylaluminum and triisobutylaluminum are preferable.

Examples of the external electron donor compound used to produce the olefin polymerization catalyst according to the invention include an organic compound that includes an oxygen atom or a nitrogen atom. Examples of the organic compound that includes an oxygen atom or a nitrogen atom include an alcohol, a phenol and a derivative thereof, an ether, an ester, a ketone, an acid halide, an aldehyde, an amine, an amide, a nitrile, an isocyanate, and an organosilicon compound. The external electron donor compound may be an organosilicon compound that includes an Si—O—C linkage, an aminosilane compound that includes an Si—N—C linkage, or the like.

Examples of the external electron donor compound used to produce the olefin polymerization catalyst according to the invention include one or more organosilicon compounds selected from organosilicon compounds represented by a general formula (2),

$$R^2{}_q Si(OR^3)_{4-q} \qquad (2)$$

wherein $R^2$ is an alkyl group having 1 to 12 carbon atoms, a cycloalkyl group having 3 to 12 carbon atoms, a phenyl group, a vinyl group, an allyl group, an aralkyl group, an alkylamino group having 1 to 12 carbon atoms, or a dialkylamino group having 1 to 12 carbon atoms, provided that a plurality of $R^2$ are either identical to or different from each other when a plurality of $R^2$ are present, $R^3$ is an alkyl group having 1 to 12 carbon atoms, a cycloalkyl group having 3 to 6 carbon atoms, a phenyl group, a vinyl group, an allyl group, or an aralkyl group, provided that a plurality of $R^3$ are either identical to or different from each other when a plurality of $R^3$ are present, and q is an integer from 0 to 3.

The olefin polymerization catalyst according to the invention may be produced by bringing (α) the solid catalyst component for olefin polymerization obtained by the production method according to the invention, (β) the organoaluminum compound, and (γ) the external electron donor compound into contact with each other using a known method.

The olefin polymerization catalyst according to the invention may be produced by bringing the solid catalyst component for olefin polymerization according to the invention, the organoaluminum compound, and the external electron donor compound into contact with each other in the absence of an olefin, or may be produced by bringing the solid catalyst component for olefin polymerization according to one embodiment of the invention, the organoaluminum compound, and the external electron donor compound into contact with each other in the presence of an olefin (i.e., in the polymerization system).

A method for producing an olefin polymer according to the invention is described below.

The method for producing an olefin polymer according to the invention includes polymerizing an olefin in the presence of the olefin polymerization catalyst according to the invention.

The olefin that is polymerized using the method for producing an olefin polymer according to the invention may be one or more olefins selected from ethylene, propylene, 1-butene, 1-pentene, 4-methyl-1-pentene, vinylcyclohexane, and the like. Among these, ethylene, propylene, and 1-butene are preferable, and propylene is more preferable.

Propylene may be copolymerized with another olefin. It is preferable to subject propylene and another α-olefin to block copolymerization. A block copolymer obtained by block copolymerization is a polymer that includes two or more segments in which the monomer composition changes sequentially. A block copolymer obtained by block copolymerization has a structure in which two or more polymer chains (segments) that differ in primary polymer structure (e.g., type of monomer, type of comonomer, comonomer composition, comonomer content, comonomer arrangement, and stereoregularity) are linked within one molecular chain.

The olefin that is copolymerized with propylene is preferably an α-olefin having 2 to 20 carbon atoms (excluding propylene having 3 carbon atoms). Specific examples of the olefin include ethylene, 1-butene, 1-pentene, 4-methyl-1-pentene, vinylcyclohexane, and the like. These olefins may be used either alone or in combination. Among these, ethylene and 1-butene are preferable.

When implementing the method for producing an olefin polymer according to the invention, the olefin may be polymerized in the presence or absence of an organic solvent, and may be used in a gaseous state or a liquid state.

The olefin is polymerized in a reactor (e.g., autoclave) in the presence of the olefin polymerization catalyst according to the invention while heating and pressurizing the mixture, for example.

When implementing the method for producing an olefin polymer according to the invention, the polymerization temperature is normally set to 200° C. or less. The polymerization temperature is preferably set to 60 to 100° C., and more preferably 70 to 90° C., from the viewpoint of improving activity and stereoregularity. When implementing the method for producing an olefin polymer according to the invention, the polymerization pressure is preferably set to 10 MPa or less, and more preferably 5 MPa or less.

A continuous polymerization method or a batch polymerization method may be used. The polymerization reaction may be effected in a single step, or may be effected in two or more steps.

When implementing the method for producing an olefin polymer according to the invention, preliminary polymerization may be effected by bringing some or all of the components of the olefin polymerization catalyst according to the invention into contact with the olefin before polymerizing the olefin (hereinafter may be appropriately referred to as "main polymerization"). It is possible to improve the catalytic activity, and easily improve the stereoregularity, the particle properties, and the like of the resulting polymer by effecting the preliminary polymerization.

The invention thus provides a novel method that can produce an olefin polymer that exhibits a high MFR, high stereoregularity, and excellent rigidity while achieving high yield.

Polymer Stereoregularity

A poly-α-olefin that is produced using the solid catalyst component for olefin polymerization obtained by the production method according to the invention preferably has a xylene-soluble content (XS) (stereoregularity of α-olefin monomer chain) of 1.5 wt % or less, more preferably 1.0 mass % or less, and particularly preferably 0.8 wt % or less.

EXAMPLES

The invention is further described below by way of examples. Note that the following examples are for illustration purposes only, and the invention is not limited to the following examples.

Example 1

1. Synthesis of Solid Catalyst Component
(1) First Step

A 500 ml round bottom flask equipped with a stirrer in which the internal atmosphere had been sufficiently replaced by nitrogen gas, was charged with 40 ml of titanium tetrachloride and 60 ml of toluene (SP=8.9) to prepare a mixed solution. A suspension prepared using 20 g (175 mmol) of spherical diethoxymagnesium, 80 ml of toluene, and 1.8 ml (7.8 mmol) of di-n-propyl phthalate was added to the mixed solution and heated to 110° C. 3.6 ml (15.5 mmol) of di-n-propyl phthalate was added stepwise to the mixture while heating the mixture. After reacting the mixture at 110° C. for 2 hours with stirring, the reaction mixture was allowed to stand, and the supernatant liquid was removed to obtain a reaction product slurry. After the addition of 187 ml of toluene (SP=8.9) to the reaction product slurry, the mixture was stirred and allowed to stand, and the supernatant liquid was removed. This operation was performed four times to wash the reaction product to obtain a reaction product slurry including a solid component (I).

(2) Second Step 170 ml of toluene (SP=8.9) and 30 ml of titanium tetrachloride were added to the reaction product slurry including the solid component (I). The mixture was heated to 110° C., and reacted for 2 hours with stirring. After completion of the reaction, the supernatant liquid was removed. 180 ml of toluene (SP=8.9) and 20 ml of titanium tetrachloride=were added to the above reaction products and the mixture was heated to 80° C. and after that 0.5 ml (2.2 mmol) of di-n-propyl phthalate was added heated to 110° C., and reacted for 2 hours with stirring. The resulting reaction mixture was allowed to stand, and the supernatant liquid was removed to obtain a reaction product slurry. After completion of the reaction, 187 ml of toluene was added to the reaction product slurry, the mixture was stirred and allowed to stand, and the supernatant liquid was removed.

This operation was performed twice to obtain a reaction product slurry including a solid component (II).

(3) Third Step 187 ml of toluene was added to the reaction product slurry including the solid component (II) to adjust the concentration of titanium tetrachloride in the reaction mixture to 1.3 wt %, and the mixture was heated to 80° C. After the addition of 0.5 ml (2.5 mmol) of diethyl phthalate, the mixture was heated to 100° C., and reacted for 1 hour with stirring. The resulting reaction mixture was allowed to stand, and the supernatant liquid was removed to obtain a reaction product slurry including a solid component (III).

(4) Fourth Step

After the addition of 150 ml of o-dichlorobenzene (SP=10.0) to the reaction product slurry including a solid component (III), the mixture was stirred at 90° C. for 1 hour, and allowed to stand, and the supernatant liquid was removed. This operation was performed twice to obtain a reaction product slurry.

After the addition of 150 ml of n-heptane (SP=7.4) to the reaction product, the mixture was stirred, and allowed to stand, and the supernatant liquid was removed. This operation was performed seven times to wash the reaction product to obtain about 20 g of a solid catalyst component (A1) for olefin polymerization.

The solid catalyst component (A1) had a magnesium atom content of 19.9 wt %, a titanium atom content of 1.2 wt %, and a total phthalic acid diester content of 16.8 wt %.

The titanium content, and the content of the internal electron donor compound in the solid were measured as described below.

Titanium Content in Solid

The titanium content in the solid was measured in accordance with JIS G1319. Content of electron donor compound in solid The content of the electron donor compound in the solid was measured using a gas chromatograph ("GC-14B" manufactured by Shimadzu Corporation) under the following conditions. The number of moles of each component was calculated from the gas chromatography measurement results using a calibration curve that was drawn in advance using the measurement results at a known concentration.

Measurement Conditions

Column: packed column (2.6 (diameter)×2.1 m, Silicone SE-30 10%, Chromosorb WAW DMCS 80/100, manufactured by GL Sciences Ltd.)

Detector: flame ionization detector (FID)

Carrier gas: helium, flow rate: 40 ml/min

Measurement temperature: vaporization chamber: 280° C., column: 225° C., detector: 280° C.

2. Production of Polymerization Catalyst, and Polymerization

An autoclave (internal volume: 2.0 l) equipped with a stirrer in which the internal atmosphere had been completely replaced by nitrogen gas, was charged with 1.32 mmol of triethylaluminum, 0.13 mmol of diethylaminotriethoxysilane (DEATES), and the solid catalyst component (A1) (0.0013 mmol on a titanium atom basis) to produce an olefin polymerization catalyst.

The autoclave was charged with 5.0 l of hydrogen gas and 1.4 l of liquefied propylene. After effecting preliminary polymerization at 20° C. for 5 minutes under a pressure of 1.1 MPa, a polymerization reaction was effected at 70° C. for 1 hour under a pressure of 3.5 MPa to obtain a propylene polymer (polypropylene).

The polymerization activity per gram of the solid catalyst component during the polymerization reaction, the p-xylene-soluble content (XS) in the polymer, the melt flow rate (MFR) of the polymer, and the flexural modulus (FM) of the polymer were measured as described below. The results are listed in Table 1.

Polymerization Activity Per Gram of Solid Catalyst Component

The polymerization activity per gram of the solid catalyst component was calculated using the following expression.

Polymerization activity ($g$–$pp$/$g$–catalyst)=weight ($g$) of polymer/weight ($g$) of solid catalyst component Melt Flow Rate (MFR) of Polymer The melt flow rate (MFR) (melt flow index) of the polymer was measured in accordance with ASTM D1238 (JIS K 7210).

Xylene-Soluble Content (XS) in Polymer

A flask equipped with a stirrer was charged with 4.0 g of the polymer (polypropylene) and 200 ml of p-xylene. The external temperature was increased to be equal to or higher than the boiling point (about 150° C.) of xylene, and the polymer was dissolved over 2 hours while maintaining p-xylene contained in the flask at a temperature (137 to 138° C.) lower than the boiling point. The solution was cooled to 23° C. over 1 hour, and an insoluble component and a soluble component were separated by filtration. A solution including the soluble component was collected, and p-xylene was evaporated by heating (drying) under reduced pressure. The weight of the residue was calculated, and the relative ratio (wt %) with respect to the polymer (propylene) was calculated to determine the xylene-soluble content (XS).

Flexural modulus (FM) of polymer

The polymer was injection-molded to prepare a property measurement specimen in accordance with JIS K 7171. The specimen was conditioned in a temperature-controlled room maintained at 23° C. for 144 hours or more, and the flexural modulus (FM) (MPa) was measured using the specimen provided that a liquid/powder exudate was not observed on the surface thereof.

Example 2

A solid catalyst component was synthesized, a polymerization catalyst was produced, and polymerization was effected in the same manner as in Example 1, except that an operation that adds 150 ml of o-dichlorobenzene (SP=10.0) to the reaction product slurry, stirs the mixture at 100° C. for 2 hours, allows the resulting reaction mixture to stand, and removes the supernatant liquid, was performed once, instead of performing the operation that adds 150 ml of o-dichlorobenzene to the reaction product slurry, stirs the mixture at 90° C. for 1 hour, allows the resulting reaction mixture to stand, and removes the supernatant liquid, twice (see "(4) Fourth step" in "1. Synthesis of solid catalyst component"). The results are listed in Table 1.

Example 3

A solid catalyst component was synthesized, a polymerization catalyst was produced, and polymerization was effected in the same manner as in Example 1, except that 0.5 ml (2.0 mmol) of dimethyl diisobutylmalonate was used instead of 0.5 ml (2.2 mmol) of di-n-propyl phthalate (see "(2) Second step" in "1. Synthesis of solid catalyst component"). The results are listed in Table 1.

Comparative Example 1

A solid catalyst component was synthesized, a polymerization catalyst was produced, and polymerization was effected in the same manner as in Example 1, except that the fourth step was omitted (see "1. Synthesis of solid catalyst component"). The results are listed in Table 1.

Comparative Example 2

A solid catalyst component was synthesized, a polymerization catalyst was produced, and polymerization was effected in the same manner as in Example 1, except that 150 ml of toluene (SP=8.9) was used instead of 150 ml of ODCB (SP=10.0) (see "(4) Fourth step" in "1. Synthesis of solid catalyst component"). The results are listed in Table 1.

Comparative Example 3

A solid catalyst component was synthesized, a polymerization catalyst was produced, and polymerization was effected in the same manner as in Example 1, except that 150 ml of 1,2-dichloropropane (SP=9.0) was used instead of 150 ml of ODCB (see "(4) Fourth step" in "1. Synthesis of solid catalyst component"). The results are listed in Table 1.

TABLE 1

|  | Ti (wt %) | Total Int. Donor (wt %) | Yeild (g-PP/ g-cat) | XS (wt %) | MFR (g/10 min) | FM (MPa) |
| --- | --- | --- | --- | --- | --- | --- |
| Example 1 | 1.2 | 17.1 | 45,800 | 0.9 | 190 | 1,860 |
| Example 2 | 1.6 | 16.4 | 45,000 | 0.8 | 200 | 1,830 |
| Example 3 | 1.4 | 16.3 | 43,300 | 0.9 | 190 | 1,810 |
| Comparative Example 1 | 2.3 | 16.2 | 46,200 | 1.1 | 230 | 1,760 |
| Comparative Example 2 | 1.5 | 16.7 | 34,600 | 1.3 | 170 | 1,780 |
| Comparative Example 3 | 1.7 | 16.0 | 49,900 | 1.3 | 160 | 1,760 |

Since the solid catalyst component for olefin polymerization produced by the production method according to the invention is brought into contact with a magnesium compound, a tetravalent titanium halide compound, and one or more first internal electron donor compound to effect a reaction, and sequentially washed with a first inert organic wash solvent having an SP of 8.0 to 9.0, a second inert organic wash solvent comprising a hydrocarbon compound having an SP of more than 9.0, and a third inert organic wash solvent having an SP of less than 8.0 after completion of the reaction process, the solid catalyst component exhibits low adhesion to a support and a low interaction with an internal donor, and a Ti species having low stereospecificity has been efficiently removed. Therefore, the solid catalyst component can produce an olefin polymer that exhibits a high rigidity of 1,800 MPa or more while maintaining high stereoregularity (i.e., can produce an olefin polymer that exhibits both high stereoregularity and high rigidity).

Since the solid catalyst components for olefin polymerization produced by the production methods of Comparative Examples 1 to 3 are not washed with a second inert organic wash solvent comprising a hydrocarbon compound having an SP of more than 9.0, or are not sequentially washed with a first inert organic wash solvent having an SP of 8.0 to 9.0, a second inert organic wash solvent comprising a hydrocarbon compound having an SP of more than 9.0, and a third inert organic wash solvent having an SP of less than 8.0, a Ti species having low stereospecificity may remain in the solid catalyst component, or the balance between stereoregularity and rigidity deteriorates (i.e., it is impossible to produce an olefin polymer that exhibits both high stereoregularity and high rigidity).

The invention claimed is:

1. A method for producing a solid catalyst component for olefin polymerization comprising:
   bringing a magnesium compound, a titanium halide compound, and one or more internal electron donor compounds into contact with each other to effect a reaction;
   washing the resulting product with a first inert organic wash solvent that does not have reactivity with the titanium halide compound, and has a solubility parameter (SP) of 8.0 to 9.0;
   washing the resulting intermediate product one or more times in the absence of the titanium halide compound with a second inert organic wash solvent that comprises a hydrocarbon compound and does not have reactivity with the titanium halide compound, but has a solubility parameter (SP) of more than 9.0; and
   washing the resulting product one or more times in the absence of the titanium halide compound with a third inert organic wash solvent that does not have reactivity with the titanium halide compound, and has a solubility parameter (SP) of less than 8.0.

2. The method for producing a solid catalyst component for olefin polymerization according to claim 1, wherein the first inert organic wash solvent is one or more compounds selected from an aromatic hydrocarbon and an aliphatic hydrocarbon.

3. The method for producing a solid catalyst component for olefin polymerization according to claim 1, wherein the second inert organic wash solvent is a halogen-containing hydrocarbon.

4. An olefin polymerization catalyst produced by producing a solid catalyst component for olefin polymerization using the method according to claim 1, and bringing an organoaluminum compound represented by a general formula (1) into contact with the solid catalyst component, $$R^1_p AlQ_{3-p} \tag{1}$$

wherein $R^1$ is an alkyl group having 1 to 6 carbon atoms, Q is a hydrogen atom or a halogen atom, and p is a real number that satisfies $0<p\leq 3$, provided that a plurality of $R^1$ are either identical to or different from each other when a plurality of $R^1$ are present.

5. The olefin polymerization catalyst according to claim 4, the olefin polymerization catalyst being produced by further bringing an external electron donor compound into contact with the solid catalyst component and the organoaluminum compound.

6. The olefin polymerization catalyst according to claim 5, wherein the external electron donor compound is one or more organosilicon compounds selected from organosilicon compounds represented by a general formula (2), $$R^2_q Si(OR^3)_{4-q} \tag{2}$$

wherein $R^2$ is an alkyl group having 1 to 12 carbon atoms, a cycloalkyl group having 3 to 12 carbon atoms, a phenyl group, a vinyl group, an allyl group, an aralkyl group, an alkylamino group having 1 to 12 carbon atoms, or a dialkylamino group having 1 to 12 carbon atoms, provided that a plurality of $R^2$ are either identical to or different from each other when a plurality of $R^2$ are present, $R^3$ is an alkyl group having 1 to 12 carbon atoms, a cycloalkyl group having 3 to 6 carbon atoms, a phenyl group, a vinyl group, an allyl group, or an aralkyl group, provided that a plurality of $R^3$ are either identical to or different from each other when a plurality of $R^3$ are present, and q is an integer from 0 to 3.

7. A method for producing an olefin polymer comprising polymerizing an olefin in the presence of the olefin polymerization catalyst according to claim 4.

8. The method for producing an olefin polymer according to claim 7, wherein the olefin is propylene.

9. An olefin polymerization catalyst produced by producing a solid catalyst component for olefin polymerization using the method according to claim 2, and bringing an organoaluminum compound represented by a general formula (1) into contact with the solid catalyst component, $$R^1_p AlQ_{3-p} \tag{1}$$

wherein $R^1$ is an alkyl group having 1 to 6 carbon atoms, Q is a hydrogen atom or a halogen atom, and p is a real number that satisfies $0<p\leq 3$, provided that a plurality of $R^1$ are either identical to or different from each other when a plurality of $R^1$ are present.

10. An olefin polymerization catalyst produced by producing a solid catalyst component for olefin polymerization using the method according to claim 3, and bringing an organoaluminum compound represented by a general formula (1) into contact with the solid catalyst component, $$R^1_p AlQ_{3-p} \tag{1}$$

wherein $R^1$ is an alkyl group having 1 to 6 carbon atoms, Q is a hydrogen atom or a halogen atom, and p is a real number that satisfies $0<p\leq 3$, provided that a plurality of $R^1$ are either identical to or different from each other when a plurality of $R^1$ are present.

11. A method for producing an olefin polymer comprising polymerizing an olefin in the presence of the olefin polymerization catalyst according to claim 5.

12. A method for producing an olefin polymer comprising polymerizing an olefin in the presence of the olefin polymerization catalyst according to claim 6.

* * * * *